United States Patent [19]

Ascione et al.

[11] Patent Number: 5,756,074
[45] Date of Patent: May 26, 1998

[54] COMPOSITIONS BASED ON AN ABRASIVE SYSTEM AND ON A SURFACTANT SYSTEM

[75] Inventors: Jean-Marc Ascione, Paris; Pascal Sterlé, Soisy S/Montmorency, both of France

[73] Assignee: L'Oreal, Paris, France

[21] Appl. No.: 590,460

[22] Filed: Jan. 23, 1996

[30] Foreign Application Priority Data

Jan. 30, 1995 [FR] France .................. 95 01039

[51] Int. Cl.$^6$ .............. A61K 7/16; A61K 7/18; A61K 7/22; A61K 9/68
[52] U.S. Cl. .............. 424/52; 424/48; 424/49; 424/54
[58] Field of Search .......................... 404/49–58

[56] References Cited

U.S. PATENT DOCUMENTS

| | | | |
|---|---|---|---|
| 3,578,719 | 5/1971 | Kalodssis et al. | 260/611 |
| 3,821,372 | 6/1974 | Vanlerberghe et al. | 424/170 |
| 4,582,702 | 4/1986 | Grollier | 424/52 |
| 4,828,824 | 5/1989 | Grollier | 424/52 |
| 4,837,008 | 6/1989 | Rudy et al. | 424/53 |
| 4,897,258 | 1/1990 | Rudy et al. | 424/53 |
| 4,963,535 | 10/1990 | Sebag et al. | 514/54 |
| 4,971,782 | 11/1990 | Rudy et al. | 424/53 |
| 4,980,078 | 12/1990 | Verite et al. | 252/118 |
| 5,087,443 | 2/1992 | Chizat et al. | 424/47 |
| 5,180,584 | 1/1993 | Sebag | 424/401 |
| 5,202,112 | 4/1993 | Prencipe | 424/52 |
| 5,334,375 | 8/1994 | Babi et al. | 424/52 |

FOREIGN PATENT DOCUMENTS 2 163 348  2/1986  United Kingdom.

*Primary Examiner*—Shep K. Rose
*Attorney, Agent, or Firm*—Finnegan, Henderson, Farabow, Garrett & Dunner, L.L.P.

[57] ABSTRACT

New compositions comprising an abrasive system comprising an alkali metal bicarbonate and a surfactant system comprising a non-ionic poly(hydroxypropyl ether) surfactant, which are characterized in that the said surfactant system further comprises an alkali metal, alkaline-earth metal or ammonium lauryl sulphate, particularly a sodium lauryl sulphate or a magnesium lauryl sulphate. Such compositions are in particular oral hygiene compositions.

The invention also relates to the use of these compositions as, or for the manufacture of, a dentifrice in the form of a paste, a gel, a liquid or a chewing gum.

25 Claims, No Drawings

COMPOSITIONS BASED ON AN ABRASIVE SYSTEM AND ON A SURFACTANT SYSTEM

The present invention relates to new compositions comprising an abrasive system including at least one alkali metal bicarbonate and a surfactant system including at least one non-ionic poly(hydroxypropyl ether) surfactant, as well as an alkali metal, alkaline-earth metal, or ammonium lauryl sulphate, these compositions being represented in particular by compositions for oral hygiene.

The invention also relates to the use of said compositions as, or for the manufacture of, a dentifrice in the form of a paste, a gel, a liquid, or a chewing gum.

Use is commonly made, in the field of oral hygiene, and particularly of dentifrices, of alkali metal bicarbonates, in particular for neutralizing the acids responsible for caries and for providing abrasiveness.

Moreover, to formulate dentifrices, use has until now been made of surface-active agents of anionic type, the role of which is to introduce both a satisfactory foaming power and a satisfactory detergent power.

Mention may more particularly be made, among the latter, of sodium lauryl sulphate, which is indeed the most widely used.

These dentifrices containing lauryl sulphate are not always readily tolerated by the surface layers of the oral epithelium, this being all the more of a problem since the use of dentifrices, as everyone knows, is repetitive.

Moreover, several cases of allergies have been reported in the literature (Barkvoll P. and Rolla G., "Possible Effects of Sodium Lauryl Sulfate on the Oral Mucosa",—J. of Dental Research—1989—vol. 68/Special issue, Abstract 996, page 991) and, indeed, the inventors have observed, following laboratory experiments, that formulations containing alkali metal bicarbonate(s) and lauryl sulphate, in particular sodium lauryl sulphate, exhibited a not insignificant irritancy towards the oral mucosa.

The inventors have described in French Patent Application No. 94 14862, foreign language counterpart to U.S. patent application Ser. No. 08/569,614, filed Dec. 8, 1995, compositions comprising, in an aqueous vehicle, an abrasive system containing at least one alkali metal bicarbonate and a surfactant system comprising at least one non-ionic poly(hydroxypropyl ether) surfactant and use of said compositions for oral hygiene, in particular dentifrices. Such compositions have the advantage of possessing an abrasiveness which is much greater than that of the previously known compositions comprising alkali metal bicarbonate and sodium lauryl sulphate, while retaining an excellent foaming and detergent power.

Following additional experiments carried out on the composition described in the abovementioned patent application, in particular for evaluating their tolerance by the oral mucosa, the inventors observed that said compositions were additionally less irritating than those of the prior art comprising alkali metal bicarbonate and sodium lauryl sulphate, but that improving the tolerance factor further would be desirable.

In continued research, the inventors have now discovered, entirely unexpectedly and surprisingly, that the addition of an alkali metal lauryl sulphate, alkaline-earth metal lauryl sulphate, or ammonium lauryl sulphate, to compounds comprising an abrasive system including at least one alkali metal bicarbonate and a surfactant system including at least one non-ionic poly(hydroxypropyl ether) surfactant made it possible to greatly decrease the irritancy of said compositions with respect to the oral mucosa.

The subject of the present invention is therefore new compositions of the type comprising an abrasive system containing one or a number of alkali metal bicarbonate(s) and a surfactant system containing one or a number of poly(hydroxypropyl ether) surfactant(s), which are characterized in that the said surfactant system further comprises at least one alkali metal lauryl sulphate, alkaline-earth metal lauryl sulphate, or ammonium lauryl sulphate.

Another subject of the present invention is compositions of this type for an oral use, in particular dentifrices.

Another subject of the present invention is compositions as, or for the manufacture of, a dentifrice which can be in the form of a paste, a gel, a liquid or a chewing gum.

However, other characteristics, aspects, subjects and advantages of the invention will become still more clearly apparent on reading the description and the examples which follow.

The at least one alkali metal bicarbonate which can be used according to the invention is preferably chosen from sodium bicarbonate or potassium bicarbonate.

Among lauryl sulphates, sodium lauryl sulphate, magnesium lauryl sulphate and ammonium lauryl sulphate are advantageously preferred, and sodium lauryl sulphate is even more particularly preferred.

The surfactants of poly(hydroxypropyl ether) type are products which are already known per se.

Preferably, according to the present invention, the non-ionic poly(hydroxypropyl ether) surfactant(s) are chosen from the compounds of following structures:

(A) The compounds corresponding to the formula (I):

in which the

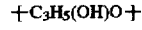

group represents the following structures (I.a), (I.b) and (I.c), taken together or separately:

and R and n have, together, one of the meanings below:

(a) R denotes a $C_{10}$–$C_{14}$ alkyl radical or a mixture of $C_{10}$–$C_{14}$ alkyl radicals, and n is a whole or decimal number varying from 2 to 10 and preferably from 3 to 6;

(b) R denotes a group of formula (II):

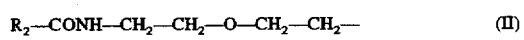

in which $R_2$ denotes a $C_{11}$–$C_{17}$ alkyl or alkenyl radical or a mixture of $C_{11}$–$C_{17}$ alkyl and/or alkenyl radicals, and n denotes a whole or decimal number varying from 1 to 5 and preferably from 1.5 to 4; or (c) R denotes a group of formula (III):

in which $R_3$ denotes a $C_7-C_{21}$ aliphatic, cycloaliphatic or arylaliphatic radical, and their mixtures, the aliphatic chains denoting in particular alkyl chains which can contain from 1 to 6 ether, thioether and/or hydroxymethylene groups, and n denotes a whole or decimal number varying from 1 to 10.

These surfactants of formula (I) can be prepared according to the processes described in French Patents FR 1,477,048, 2,328,763, French language counterpart to U.S. Pat. No. 4,307,079, and 2,091,516, French language counterpart to U.S. Pat. No. 3,821,372, the disclosures of which are specifically incorporated by reference herein.

(B) The compounds prepared by condensation at a temperature ranging from 50° to 120° C., of 2 to 10 and preferably of 2.5 to 6 mole of glycidol per mole of alcohol or of alpha-diol containing 10 to 14 carbon atoms, the glycidol being slowly added to the alcohol or to the alpha-diol. The process for the preparation of these compounds in described in French Patent FR 2,169,787, French language counterpart to U.S. Pat. No. 4,515,775, the disclosure of which is specifically incorporated by reference herein.

(C) The compounds prepared by polyaddition of glycerol monocholorohydrin to a polyhydroxylated organic compound in the presence of a strong base, with the removal of the water, by distillation, as it is formed. A base is considered strong at a pH greater than 10. These compounds are described in French Patent FR 2,574,786, French language counterpart to U.S. Pat. No. 4,677,232, the disclosure of which is specifically incorporated by reference herein.

The more particularly preferred compounds according to the invention, among the non-ionic poly(hydroxypropyl ether) surfactants described in paragraphs (A), (B), and (C) above, are:

i) those of following formulae (IV) and (V):

in which formula (V) $R_1$ denotes a mixture of $C_{10}H_{21}$, and $C_{12}H_{25}$ alkyl radicals;

ii) the compounds prepared by condensation of 3.5 mole of glycidol with an alpha-diol having 12 carbon atoms, according to the process described in French Patent FR 2,091,516, French language counterpart to U.S. Pat. No. 3,821,372, the disclosure of which is specifically incorporated by reference herein;

iii) the compounds of formula (VI):

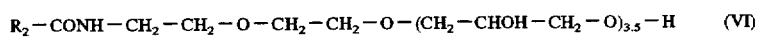

in which $R_2$ denotes a mixture of radicals comprising the following alkyl and alkenyl radicals: $C_{11}H_{23}$, $C_{13}H_{27}$, the radicals derived from coconut fatty acids and the radical derived from oleic acid; or iv) the compounds prepared by condensation of 3.5 mole of glycidol with a mixture of $C_{11}-C_{14}$ alpha-diols described in French Patent FR 2,091,516, French language counterpart to U.S. Pat. No. 3,821,372, the disclosure of which is specifically incorporated by reference herein.

Dodecanediol polyglycerolated with 3.5 mole of glycerol is more particularly preferred.

In the compositions according to the invention, the alkali metal bicarbonate(s) are generally present in concentrations by weight ranging from approximately 0.5 to 80% and preferably from approximately 1 to 50%, the non-ionic poly(hydroxypropyl ether) surfactant(s) are generally present in concentrations by weight ranging from approximately 0.01 to 10% and preferably from approximately 0.05 to 5%, and the alkali metal lauryl sulphate, alkaline-earth metal lauryl sulphate or ammonium lauryl sulphate is generally present in concentrations by weight ranging from approximately 0.01 to 10% and preferably from approximately 0.05 to 5%, all these concentrations by weight being expressed with respect to the total weight of the composition.

The compositions in accordance with the invention which are intended for oral hygiene can, for example, contain, in addition to the alkali metal bicarbonate(s), the non-ionic poly(hydroxypropyl ether) surfactant(s), and the alkali metal lauryl sulphate, alkaline-earth metal lauryl sulphate or ammonium lauryl sulphate(s), as a simple vehicle (bulking agent) or for their own activity, excipients or ingredients commonly used in products for oral use.

Of course, care will be taken to choose these complementary compounds so that the advantageous properties associated with the ternary combination in accordance with the invention are not, or are substantially not, adversely affected by the envisaged addition.

Compositions in accordance with the invention can be prepared according to the usual processes corresponding to the vehicles chosen. The physiologically acceptable vehicle can be different in nature according to the form chosen for the composition: for example, optionally thickened aqueous or aqueous/alcoholic medium, pasty or solid excipient, or gum.

Depending upon the desired forms, these compositions can also contain other abrasive agents, among which mention may be made of, for example, silica, alumina, calcium hydrogenphosphate and calcium carbonate, anticarious agents such as, for example, sodium or potassium or amine fluorides or sodium monofluorophosphate, antibacterial agents such as, for example, chlorhexidine, alexidine, hexetidine, cetylpyridinium chloride or 2,4,4'-trichloro-2'-hydroxydiphenyl ether, antiinflammatory agents, antihalitosis agents, agents for combatting stains and/or tartar, agents for combatting free radicals, anti-oxidants, enzymes, vitamins, trace elements, haemostatic agents, healing agents and agents which are active on the gum.

Moreover, they can contain other usual agents such as binding agents, sweeteners, humectants or fresheners, preservatives, dyes, fragrances, flavouring agents, peptizing agents and plasticizers.

Concrete, but in no way limiting, examples illustrating the invention will now be given.

EXAMPLE 1

The irritancy with respect to the oral mucosa of three aqueous dispersions defined below (S1, S2 and S3) was measured according to the "in vitro" test described in the publication J.A.O.C.S.—1989—vol. 66 No. 9, entitled: "An in vitro Method for Evaluation of the Irritancy of Anionic Surfactants", by the authors A. S. Anavkar and C. V. Natraj, the principle of the test consisting in extracting, by the test solution, a blue dye (Coomassie Brilliant Blue R 250) trapped in a protein matrix (gelatin) and in quantifying the amount of dye thus extracted by measuring the absorbence of the final solution by spectrophotometry.

The lower the amount of dye extracted, the lower the absorbence and the lower the irritancy.

For each of the test solutions, the absorbencies obtained, measured at 590 nm, were as follows:

| AQUEOUS SOLUTION containing: | | | |
|---|---|---|---|
| | NaHCO$_3$ | Dodecanediol polyglycerolated with 3.5 mole of glycerol | Sodium lauryl sulphate | ABSORBENCE |
| S1 | 5% | | 1% | 0.70 |
| S2 | 5% | 1% | | 0.54 |
| S3 | 5% | 1% | 1% | 0.09 |

From these measurement results, the aqueous solution S3 according to the invention, containing 5% of sodium bicarbonate, 1% of dodecanediol polyglycerolated with 3.5 mole of glycerol and 1% of sodium lauryl sulphate, has the lowest absorbence and consequently the lowest irritancy compared to solutions S1 and S2 which are not in accordance with the present invention.

These results obtained for S2 and S3 demonstrate that the addition of sodium lauryl sulphate to a solution of sodium bicarbonate and of dodecanediol polyglycerolated with 3.5 mole of glycerol decreases the irritancy of this solution by a factor of more than 5.

These results are all the more surprising since, in comparing S1 and S3, sodium lauryl sulphate, when combined with sodium bicarbonate alone, has an irritancy which is approximately 8 times greater than the solution in accordance with the invention.

EXAMPLE 2

A toothpaste in accordance with the invention is illustrated here.

Sodium bicarbonate, Codex 0/13, sold by the company Solvay . . . 25 g
Thickening silica, sold under the name "Sident 22S" by the company Degussa . . . 9.5 g
Sodium carboxymethylcellulose, sold under the name "Blanose 9M31 F" by the company Hercules . . . 1.25 g
Sorbitol as an aqueous solution containing 70% of active material (AM) . . . 15.4 g AM
Dodecanediol polyglycerolated with 3.5 mole of glycerol . . . 0.75 g
Sodium lauryl sulphate . . . 0.75 g
Titanium dioxide . . . 0.8 g
Sodium monofluorophosphate . . . 0.8 g
Preservative, sweetener, fragrance . . . q.s.
Water . . . q.s. for 100 g

We claim:

1. A composition comprising an abrasive system including at least one alkali metal bicarbonate and a surfactant system including at least one non-ionic poly(hydroxypropyl ether) surfactant, wherein said surfactant system further comprises at least one alkali metal lauryl sulphate, alkaline-earth metal lauryl sulphate, or ammonium lauryl sulfate.

2. Composition according to claim 1 wherein said alkali metal bicarbonate is sodium bicarbonate or potassium bicarbonate.

3. Composition according to claim 1 wherein said lauryl sulphate is said alkali metal lauryl sulphate.

4. Composition according to claim 1 wherein said alkali metal lauryl sulphate is sodium lauryl sulphate.

5. Composition according to claim 1 wherein said lauryl sulphate is said alkaline-earth metal lauryl sulphate.

6. Composition according to claim 1 wherein said alkaline-earth metal lauryl sulphate is magnesium lauryl sulphate.

7. Composition according to claim 1 wherein said lauryl sulphate is ammonium lauryl sulphate.

8. Composition according to claim 1 wherein said non-ionic poly(hydroxypropyl ether) surfactant is one of the following compounds:

(A) the compounds corresponding to the formula (I):

$$RO\mathord{+}C_3H_5(OH)O]_n\mathord{-}H \qquad (I)$$

in which the $$\mathord{+}C_3H_5(OH)O\mathord{+}$$

group represents the following structures (I.a), (I.b) and (I.c), taken together or separately:

$$\mathord{+}CH_2\mathord{-}CHOH\mathord{-}CH_2\mathord{-}O\mathord{+} \qquad (I.a)$$

$$\mathord{+}CH_2\mathord{-}\underset{\underset{CH_2OH}{|}}{CHO}\mathord{+} \qquad (I.b)$$

$$\mathord{+}\underset{\underset{CH_2OH}{|}}{CH}\mathord{-}CH_2\mathord{-}O\mathord{+} \qquad (I.c)$$

and R and n have, together, one of the meanings below:

a) R denotes a $C_{10}$–$C_{14}$ alkyl radical or a mixture of $C_{10}$–$C_{14}$ alkyl radicals, and n is a whole or decimal number from 2 to 10;

b) R denotes a group of formula (II):

$$R_2\mathord{-}CONH\mathord{-}CH_2\mathord{-}CH_2\mathord{-}O\mathord{-}CH_2\mathord{-}CH_2\mathord{-} \qquad (II)$$

in which $R_2$ denotes a $C_{11}$–$C_{17}$ -alkyl or -alkenyl radical, a mixture of $C_{11}$–$C_{17}$ -alkyl radicals, a mixture of $C_{11}$–$C_{17}$-alkenyl radicals, or a mixture of $C_{11}$–$C_{17}$ -alkyl radicals and $C_{11}$–$C_{17}$ -alkenyl radicals, and n denotes a whole or decimal number from 1 to 5; or c) R denotes a group of formula (III):

$$R_3\mathord{-}CHOH\mathord{-}CH_2\mathord{-} \qquad (III)$$

in which $R_3$ denotes a $C_7$–$C_{21}$ aliphatic, $C_7$–$C_{21}$ cycloaliphatic or $C_7$–$C_{21}$ arylaliphatic radical, or a mixture of any of said $C_7$–$C_{21}$ radicals, and n denotes a whole or decimal number from 1 to 10;

(B) the non-ionic poly(hydroxypropyl ether) surfactants prepared by condensation and at a temperature ranging from 50° to 120° C., of 2 to 10 mole of glycidol per mole of either alcohol containing 10 to 14 carbon atoms or of alpha-diol containing 10 to 14 carbon atom; and (C) the non-ionic poly(hydroxypropyl ether) surfactants prepared by polyaddition of glycerol monocholorodrin to a polyhydroxylated organic compound in the presence of a strong base, with removal of the water, by distillation, as said water is formed.

9. A composition according to claim 8, wherein:

in (A) a), n is a whole or decimal number from 3 to 6;
in (A) b), n is a whole or decimal number from 1.5 to 4;
in (A) c), the aliphatic chains denote alkyl chains which can contain from 1 to 6 ether groups, thioether groups, hydroxymethylene groups, and mixtures of any of said groups; and in (B), there are 2.5 to 6 mole of glycidol per mole of either alcohol containing 10 to 14 carbon atoms or of alpha-diol containing 10 to 14 carbon atoms.

10. Composition according to claim 8 wherein said non-ionic poly(hydroxypropyl ether) surfactant is one of the following compounds:

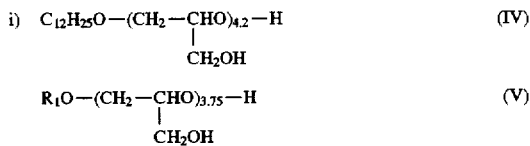

in which formula (V) $R_1$ denotes a mixture of $C_{10}H_{21}$, and $C_{12}H_{25}$ alkyl radicals;

ii) the compounds prepared by condensation of 3.5 mole of glycidol with an alpha-diol having 12 carbon atoms;

iii) the compounds of formula (VI):

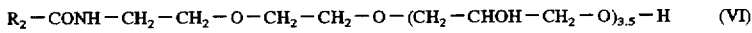

in which $R_2$ denotes a mixture of radicals comprising the following alkyl and alkenyl radicals: $C_{11}H_{23}$, $C_{13}H_{27}$, the radicals derived from coconut fatty acids and the radical derived from oleic acid; and iv) the compounds prepared by condensation of 3.5 mole of glycidol with a mixture of $C_{11}$–$C_{14}$ alpha-diols.

11. Composition according to claim 8 wherein the non-ionic poly(hydroxypropyl ether) surfactant is a dodecanediol polyglycerolated with 3.5 mole of glycerol.

12. Composition according to claim 1 wherein at least one alkali metal bicarbonate is present in a concentration by weight ranging from 0.5 to 80% with respect to the total weight of the composition.

13. Composition according to claim 12 wherein said concentration by weight ranges from 1 to 50%.

14. Composition according to claim 1 wherein said at least one non-ionic poly(hydroxypropyl ether) surfactant is present in a concentrations by weight ranging from 0.01 to 10% with respect to the total weight of the composition.

15. Composition according to claim 14 wherein said concentration by weight ranges from 0.05 to 5%.

16. Composition according to claim 1 wherein said at least one alkali metal lauryl sulphate, alkaline-earth metal lauryl sulphate, or ammonium lauryl sulphate is present in a concentrations by weight ranging from 0.01 to 10% with respect to the total weight of the composition.

17. Composition according to claim 16 wherein said concentration ranges from 0.05 to 5% with respect to the total weight of the composition.

18. An oral hygiene composition comprising a composition according to claim 1.

19. An oral hygiene composition according to claim 18, wherein said composition is a dentifrice.

20. Composition according to claim 18 wherein said oral hygiene composition further comprises at least one physiologically acceptable ingredient.

21. Composition according to claim 1 wherein said composition further comprises at least one ingredient selected from silica, alumina, calcium hydrogenphosphate and calcium carbonate, anticarious agents, antibacterial agents, antiinflammatory agents, antihalitosis agents, agents for combatting stains and/or tartar, agents for combatting free radicals, anti-oxidants, enzymes, vitamins, trace elements, haemostatic agents, and healing agents.

22. Composition according to claim 21 wherein said anticarious agents are sodium, potassium, amine fluorides, and sodium monofluorophosphate.

23. Composition according to claim 21 wherein said antibacterial agents are chlorhexidine, alexidine, hexetidine, cetylpyridinium chloride and 2,4,4'-trichloro-2'-hydroxydiphenyl ether.

24. Compositions according to claim 21 wherein said composition further comprises at least one ingredient selected from binding agents, sweeteners, humectants or fresheners, preservatives, dyes, fragrances, flavouring agents, peptizing agents and plasticizers.

25. A method of making a liquid dentifrice, a toothpaste, a tooth gel or a chewing gum comprising the step of including in said liquid dentifrice, toothpaste, tooth gel or chewing gum the composition according to claim 1.

* * * * *

UNITED STATES PATENT AND TRADEMARK OFFICE
CERTIFICATE OF CORRECTION

PATENT NO. : 5,756,074
DATED : May 26, 1998
INVENTOR(S) :
Jean-Marc ASCIONE et al.

It is certified that error appears in the above-indentified patent and that said Letters Patent is hereby corrected as shown below:

In claim 8, col. 6, line 54, "atom" should read --atoms--.

Signed and Sealed this

Eighteenth Day of August, 1998

*Attest:*

BRUCE LEHMAN

*Attesting Officer*       *Commissioner of Patents and Trademarks*